United States Patent
Grass et al.

(10) Patent No.: US 9,335,288 B2
(45) Date of Patent: May 10, 2016

(54) STORAGE VESSEL FOR A LIQUID, AND A METHOD FOR MEASURING THE ELECTRIC CONDUCTIVITY OF A LIQUID

(75) Inventors: Philippe Grass, Regensburg (DE); Manfred Weigl, Sinzing/Viehhausen (DE)

(73) Assignee: Continental Automotive GmbH, Hannover (DE)

( * ) Notice: Subject to any disclaimer, the term of this patent is extended or adjusted under 35 U.S.C. 154(b) by 154 days.

(21) Appl. No.: 14/118,749

(22) PCT Filed: May 15, 2012

(86) PCT No.: PCT/EP2012/058998
§ 371 (c)(1),
(2), (4) Date: Nov. 19, 2013

(87) PCT Pub. No.: WO2012/159934
PCT Pub. Date: Nov. 29, 2012

(65) Prior Publication Data
US 2014/0070826 A1 Mar. 13, 2014

(30) Foreign Application Priority Data
May 20, 2011 (DE) .......................... 10 2011 102 698

(51) Int. Cl.
*G01R 27/08* (2006.01)
*G01N 27/06* (2006.01)
(Continued)

(52) U.S. Cl.
CPC .............. *G01N 27/06* (2013.01); *F01N 3/2066* (2013.01); *F01N 11/00* (2013.01); *F01N 2560/12* (2013.01); *F01N 2610/142* (2013.01); *F01N 2610/148* (2013.01); *F01N 2900/1814* (2013.01);
(Continued)

(58) Field of Classification Search
CPC .... G01N 27/021–27/025; G01N 27/06–27/10; F01N 3/2066; F01N 11/00; G01R 27/22
USPC .................................................. 324/691–724
See application file for complete search history.

(56) References Cited

U.S. PATENT DOCUMENTS 3,603,873 A * 9/1971 Cirulis ........................ 324/445
5,252,925 A * 10/1993 Matsumoto et al. .......... 324/445
(Continued)

FOREIGN PATENT DOCUMENTS

DE      21 60 547      6/1974
DE      28 37 102      3/1979
(Continued)

OTHER PUBLICATIONS

"Endress + Hauser conducta GmbH: Technische Information—Condumax W CLS21 and CLS21D—Leitfähigkeitssensoren", Jul. 30, 2007, pp. 100-107.
(Continued)

*Primary Examiner* — Jermele M Hollington
*Assistant Examiner* — Demetrius Pretlow
(74) *Attorney, Agent, or Firm* — Cozen O'Connor

(57) ABSTRACT

A storage vessel for a liquid has an arrangement for measuring the electric conductivity of the liquid situated in the vessel. The arrangement has a first contact and a second contact, which are wetted by the liquid and between which the conductivity is measured. The storage vessel has a first conductor loop with a first open end coupled electrically to the first contact and a second open end coupled electrically to the second contact.

11 Claims, 1 Drawing Sheet

(51) Int. Cl.
  *F01N 3/20*   (2006.01)
  *F01N 11/00*  (2006.01)
(52) U.S. Cl.
  CPC .......... *F01N 2900/1818* (2013.01); *Y02T 10/24* (2013.01); *Y02T 10/47* (2013.01)

(56) References Cited

U.S. PATENT DOCUMENTS

| | | | | |
|---|---|---|---|---|
| 5,767,682 | A  * | 6/1998  | Sekimoto et al. | 324/445 |
| 6,414,493 | B1 * | 7/2002  | Rezvani | 324/442 |
| 6,782,736 | B1 * | 8/2004  | Hammer | 73/61.44 |
| 2010/0300188 | A1 * | 12/2010 | Halalay et al. | 73/114.55 |
| 2011/0163756 | A1 * | 7/2011  | Wang et al. | 324/537 |
| 2011/0309087 | A1   | 12/2011 | Hodgson et al. | |

FOREIGN PATENT DOCUMENTS

| | | |
|---|---|---|
| DE | 29 821 494 | 3/1999 |
| DE | 10 2008 012 543 | 9/2009 |
| DE | 10 2009 00493 | 7/2010 |

OTHER PUBLICATIONS

Babel, et al. "Fortschritte in der Sensortechnik entlang der Technologie—Roadmap", Feb. 28, 2009, pp. 100-112.

* cited by examiner

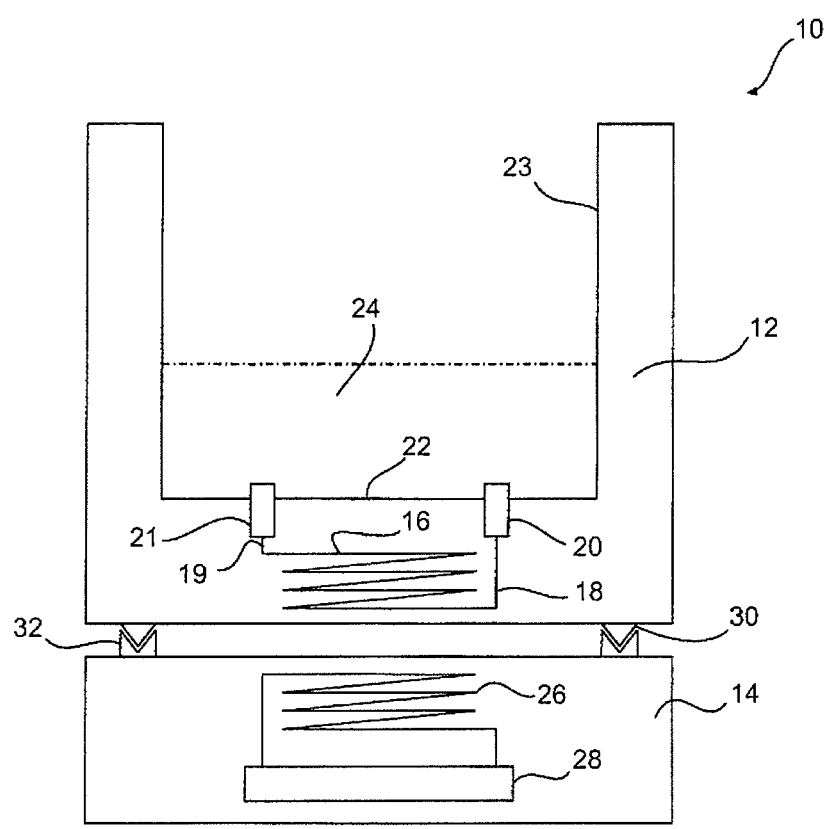

STORAGE VESSEL FOR A LIQUID, AND A METHOD FOR MEASURING THE ELECTRIC CONDUCTIVITY OF A LIQUID

CROSS-REFERENCE TO RELATED APPLICATIONS

This is a U.S. national stage of application No. PCT/EP2012/058998, filed on 15 May 2012, which claims priority to the German Application No. 10 2011 102 698.7, filed 20 May 2011, the content of both incorporated herein by reference.

BACKGROUND OF THE INVENTION

1. Field of the Invention

The invention relates to a storage vessel for a liquid, the storage vessel having an arrangement for measuring the electrical conductivity of the liquid that is located in the storage vessel, and a method for this purpose.

2. Related Art

Storage vessels for aqueous urea solutions are known. Known storage vessels comprise measuring devices, with which the electrical conductivity of the liquid that is located in the storage vessel is conductively measured. Aqueous urea solution is used, for example, in SCR systems (selective catalytic reduction systems), in order, in a catalytic process, to reduce the proportion of the nitrogen oxide in the exhaust gas from diesel engines. The aging state and/or the quality of the solution can be established by determining the conductivity of the urea solution. Conductivity measurements of the urea solution are also carried out in order to determine the fill level of the liquid in the storage vessel.

In the case of the known storage vessels, at least two electrodes are fed through the housing wall, which electrodes are in conductive contact with the liquid. The sites where these electrodes are fed through are sealed by O-rings in order to prevent liquid escaping from the storage vessel at these sites.

An electrical voltage is applied between the contacts of the storage vessel in order to measure the conductivity. If the liquid is electrically conductive, the contacts are mutually connected by way of the liquid and a current flows between the electrodes due to the electrical field. The strength of the current is representative of the conductivity of the liquid.

Plug systems or detachable cable connections are used in order to produce the electrical connection between the storage vessel and an electronic measuring device. In the case of repair or servicing, these connections are initially detached and eventually re-attached.

The presence of defects in liquid tightness and/or leakages at the feedthroughs of the electrodes is problematic in the case of the known storage vessels, in which leakages and defects in liquid tightness arise, for example, as a result of mechanical loadings. Loadings of this type occur, for example, as a result of vibrations at the installation site of the storage vessel or as a result of detaching the cable connection multiple times.

As these storage vessels are exposed to intensified vibrations and cable movements in SCR systems, material fatigue also becomes a factor in the connection cables, which leads to loose connections or cable breaks.

SUMMARY OF THE INVENTION

An object of the invention is to provide a storage vessel for liquids, the storage vessel having an arrangement for measuring the electrical conductivity of the liquid that is located in the storage vessel, and a method for measuring the electrical conductivity, which method involves the storage vessel being constructed in a particularly simple and robust manner and the method can be carried out in a simple and reliable manner.

The object is achieved in accordance with the invention by way of a storage vessel having an arrangement for measuring the electrical conductivity of the liquid that is located in the storage vessel, wherein the arrangement comprises a first contact and a second contact, which are wetted by the liquid, and the conductivity is measured between the contacts. The storage vessel comprises a first conductor loop having a first open end that is electrically coupled to the first contact, and a second open end that is electrically coupled to the second contact. If the contacts are wetted and connected by an electrically conductive liquid, a current flows between the contacts upon applying an electrical voltage. The current strength between the contacts is dependent upon the conductivity of the liquid. The conductivity of the liquid can be determined by evaluating the current strength.

In one aspect, the first conductor loop of the storage vessel is used for providing an electrical field to the contacts of the storage vessel, and in particular, an electrical voltage is generated between the contacts with the aid of this first conductor loop. The form of the first conductor loop can comprise differing dimensions. The first conductor loop can be round, in other words can embody the form of a part, semi or complete circle. It is feasible that the first conductor loop is a coil having at least one winding. The function of the first conductor loop can equally be achieved with other forms. By way of example, the first conductor loop could, according to another aspect, comprise a rectangular or polygonal form. It is also feasible that the first conductor loop is a straight or curved conductor.

According to an aspect of the present invention, the first conductor loop is formed by way of an open conductor, in other words it is not closed and comprises two open ends. The open ends of the first conductor loop are electrically coupled to the contacts of the storage vessel. The ends can be directly connected to the contacts in an electrical manner for this purpose. For an indirect coupling, additional electrical components, such as, for example, capacitors or resistors, can be installed between the open ends and the contacts.

In contrast to conventional storage vessels having arrangements for measuring the electrical conductivity of liquids, it is not necessary in the case of the storage vessel in accordance with the invention to provide a through-going contact of the contacts through the storage vessel housing to external measuring devices. Therefore it is not necessary to provide any apertures in order to produce a connection to the contacts and an electronic measuring system. Consequently, it is likewise not necessary to provide a sealing arrangement for the apertures or through-going bore holes using O-rings.

In one aspect, the storage vessel comprises a second conductor loop for inducing a voltage into the first conductor loop. The second conductor loop is used to generate a magnetic field, with which a voltage can be induced into the first conductor loop. For this purpose, the second conductor loop is excited by an input voltage. A changing magnetic field is generated using the second conductor loop by changing the amplitude of the input voltage with respect to time. If this field flows through the first conductor loop, this leads to a voltage being induced into the first conductor loop. Similar to the first conductor loop, different forms are also feasible for the second conductor loop. The second conductor loop can, for example, be embodied as a coil having at least one winding.

In a further aspect of the storage vessel, the second conductor loop is coupled to an electronic measuring system for the purpose of determining the conductivity of the liquid. A coupling arrangement means that the second conductor loop and the electronic measuring system can be directly connected in an electrical manner, for example, by way of a cable connection, alternatively the second conductor loop can, however, also be coupled in a different way to the electronic measuring system, for example, in an inductive or capacitive manner.

In accordance with an aspect of the present invention, the electronic measuring system can fulfill two functions. In its first function, the electronic measuring system is used to feed an input voltage into the second conductor loop in order to consequently generate a magnetic field using the second conductor loop. The input voltage can, for example, be an AC voltage or a sequence of voltage pulses. In its second function, the electronic measuring system is used for determining and evaluating the current flow in the first conductor loop, which current flow is generated by way of inducing a voltage into this first conductor loop.

Owing to the fact that the energy for measuring the conductivity is coupled in a conductive manner, it is not necessary to house an additional energy source, such as for example a battery, in the housing of the storage vessel. One advantage of the inductive coupling between the conductor loops also resides in the fact that both the storage vessel as well as the electronic measuring system and/or the second conductor loop can be replaced in a simple manner as required, without having to detach a cable or plug connection between the electronic measuring system and the arrangement for measuring the conductivity.

The absence of a cable connection ensures that mechanical malfunctions of electrical conductors, such as loose connections or cable breaks, do not occur.

In a further aspect, the second conductor loop is integrated into a housing, wherein the housing can be separated from the housing of the storage vessel. It is feasible, for example, that the second conductor loop is molded into a protective material. The housing could, for example, be installed into a vehicle or a part of an SCR system. It is not necessary in this case to arrange the electronic measuring system in the vicinity of the second conductor loop. It is feasible that the electronic measuring system is integrated into the system electronics of an SCR system. In comparison to the conventional storage vessels in SCR systems, the simple replaceability of the storage vessel in accordance with the invention or of the electronic measuring system is of particular advantage with regard to simple and rapid service or repair tasks.

In a further aspect, the storage vessel comprises first guiding means and the housing comprises second guiding means for positioning the second conductor loop in a pre-defined arrangement with respect to the first conductor loop. An operating position of the second conductor loop can thus be adjusted relative to the first conductor loop, which enables an optimum inductive coupling between the conductor loops.

In a further aspect, the contacts protrude into the liquid and are in electrically conducting contact with said liquid. The contacts can also be provided in a flat and even manner in a plane with a storage vessel wall or in depressions of the storage vessel wall without impairing their function. It is essential in any case that the contacts are wetted by the liquid. The contacts can be arranged at the base of the storage vessel or at the side wall of the storage vessel.

In a further aspect, the first conductor loop is embedded in a wall of the storage vessel. The arrangement of embedding the first conductor loop is used on the one hand for protecting the conductor material against contact with the liquid in the storage vessel and on the other hand for fixing the first conductor loop in a pre-defined position. The first conductor loop is, for example, protected against corrosion and short circuiting by virtue of the embedded arrangement. The first conductor loop can lie in a flat plane or be tailored to suit a contour of the housing of the storage vessel. The first conductor loop can be integrated into the storage vessel wall, for example, during production of the storage vessel using the injection molding method. The first conductor loop can also be integrated into the wall in the form of a printed electronic circuit during production of the storage vessel. It is additionally feasible that the second conductor loop is also integrated into the wall of the storage vessel.

In the case of parts of the first conductor loop being in contact with the liquid, a suitable insulating material can be used for the purpose of protecting the first conductor loop against short circuit or corrosion.

It is not necessary for the first conductor loop to be arranged in the vicinity of the contacts. It is feasible, for example, for the contacts to be arranged at the base of the storage vessel and the first conductor loop to be arranged in a side wall.

In one aspect, a wall of the storage vessel in the region of the first conductor loop has a magnitude of electrical conductivity that is less than the magnitude of the electrical conductivity of a liquid whose conductivity is to be measured. In particular, it can be lower by a factor of 10 or more. The liquid whose conductivity is to be measured is a liquid, for which the storage vessel is to be used. The conductivity of this liquid can, for example, amount to 2 mS/cm. In particular, under normal conditions (room temperature, no aging), the conductance value of aqueous urea solution amounts to approximately 2 mS/cm.

Non-electrically conductive or poorly conductive materials such as, for example, synthetic materials, are frequently used for storage vessels of this type. It can, however, be advantageous if the storage vessel or parts of the storage vessel comprise electrically conductive materials such as, for example, conductive synthetic materials, metals or alloys. In this manner, a static loading of the storage vessel or parts of the storage vessel is counteracted. It is also possible to provide a conductive storage vessel, for example made from aluminum or a different metal, with an insert made from a different material having a lower conductivity, in the region of the first conductor loop.

In another aspect, a further option for counteracting static loadings lies in encasing or surrounding the storage vessel either partially or entirely with an electrically conductive material.

A lower conductivity of the material of the storage vessel in the region of the first conductor loop can aid the inductive coupling between the first conductor loop and the second conductor loop.

In a further aspect, the first conductor loop and the second conductor loop comprise in each case a longitudinal axis and the longitudinal axes are arranged in an operating position essentially parallel to one another. Each longitudinal axis is a symmetrical axis of the respective conductor loop, in particular, an axis around which a winding of the respective conductor loop is wound. They can coincide with the main direction of a magnetic field that is generated by a current flow in the respective conductor loop. This arrangement ensures the best possible inductive coupling of the two conductor loops. It is generally provided in order to achieve a good inductive coupling that in an operating position the flux lines of the magnetic field that is generated using the second conductor loop are essentially perpendicular to the conductor or to a plane that is encased by the first conductor loop. An inclined or angled position of the axes of the conductor loops is feasible if an inductive coupling can still be achieved in this position.

In one aspect, the first conductor loop and the second conductor loop are arranged coaxially with respect to one another in an operating position. This arrangement ensures an optimal inductive coupling of the conductor loops. The second conductor loop can be arranged parallel to the first conductor loop or inside the first conductor loop. This renders it possible, for example, to embody a corresponding depression and/or contour or feedthrough in the housing of the storage vessel, in which depression and/or contour or feedthrough the second conductor loop is arranged in its operating position. The first conductor loop is, for this purpose, by way of example, arranged in the housing wall in a manner where it borders this depression and/or contour or feedthrough.

In another aspect, the storage vessel is a tank in a vehicle. It is also feasible that the storage vessel is installed in a warehouse or at a filling station.

In another aspect, the storage vessel is installed in an SCR system. For example, the storage vessel is used to contain an aqueous urea solution and is used to determine and evaluate the electrical conductivity or other characteristics of the urea solution associated with the electrical conductivity.

In accordance with another aspect of the present invention, a method is used for measuring the conductivity of a liquid in a storage vessel having the above described features. It comprises the following steps:

Inducing a voltage into the first conductor loop,
Determining the conductivity of the liquid by evaluating an induction current in the first conductor loop.

In the method in accordance with the invention, a voltage is induced into the first conductor loop, in which method a magnetic field flows through the first conductor loop or the plane that is surrounded by said conductor loop. The conductivity can, for example, be determined as a numerical value or as a relative variable. It is also possible that upon determining the conductivity merely a representative value is determined for the excess or shortfall with respect to a pre-defined limit value. It is also feasible that the electrical resistance is determined instead of the electrical conductivity.

In contrast to conventional methods in SCR systems, the conductivity of the fluid can be determined using the method in accordance with the invention without it being necessary to provide a cable connection between the evaluation unit and the storage vessel. Furthermore, this method does not require any active components such as, for example, transistors or integrated switching circuits at the first conductor loop. An energy source such as, for example, a battery that is connected to the first conductor loop, in other words with the aid of electrical conductors is also not necessary in this device and with this method. The electrical conductivity or other characteristics of the liquid are measured in order to monitor limit values or fill levels of the liquid or the storage vessel.

In comparison to known methods, the inductive coupling of the measuring arrangement provides on the one hand security against mechanical malfunctions caused by cable breaks or material fatigue, and on the other hand, prevents the risk of an incorrect connection of the measuring arrangement. As a result of this, this method and device provide protection against reverse polarity.

In one embodiment of the method, a voltage is induced into the first conductor loop by way of generating a magnetic field using a second conductor loop.

In an additional embodiment of the method in accordance with the invention, the induction current is evaluated with the aid of an electronic measuring system that is connected to the second conductor loop.

The present invention is further explained hereinunder with reference to an exemplary embodiment.

BRIEF DESCRIPTION OF THE DRAWING

The single FIG. 1 illustrates a schematic illustration of a storage vessel in accordance with the invention having a first and a second conductor loop.

DETAILED DESCRIPTION OF THE PRESENTLY PREFERRED EMBODIMENTS

In the FIGURE, like reference numerals are used for the like parts.

FIG. 1 illustrates a storage vessel 10 having an arrangement for measuring the conductivity of the liquid 24 that is located in the storage vessel. The storage vessel 10 features a housing 12 that encompasses the liquid 24, the housing having a storage vessel base 22 and side walls 23. The housing 12 can comprise at least one aperture that is used, for example, for filling the storage vessel 10 or for equalizing the pressure in the storage vessel 10. An aperture can also be used to release or remove the fluid. In FIG. 1, the housing 12 is illustrated as being open at the top, in an additional embodiment the housing 12 comprises a covering wall (not illustrated) that closes the top of the storage vessel 10.

In order, for example, to tailor the external dimensions of the storage vessel 10 to suit the installation dimensions of the provided installation space, the contour of the housing 12 can be embodied in different forms. The housing 12 can comprise devices and means for fastening the housing 12 to surrounding constructions (not illustrated). A first conductor loop 16 is embedded in the base 22 of the housing 12, which first conductor loop is coupled to its first open end 18 to the first contact 20 and its second open end 19 to the second contact 21. The first conductor loop 16 in this FIGURE is arranged centrally in the base 22. The first conductor loop can likewise be arranged (not illustrated in this FIGURE) in one of the side walls 23 or in the liquid 24. The contacts 20, 21 are located at the base 22 of the housing 12 and protrude into the liquid 24.

Furthermore, there is a housing 14 that is arranged underneath the housing 12. A second conductor loop 26 is integrated into the housing 14, which second conductor loop is connected to an electronic measuring system 28 that is likewise arranged in the housing 14. First guiding means 30, associated with the housing 12, and second guiding means 32, associated with the housing 14, cooperate with each other in order to position the housings 12 and 14 in a pre-defined arrangement. In this arrangement, the first conductor loop 16 is arranged coaxially with respect to the second conductor loop 26.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

The invention claimed is:

1. A storage vessel (10) for storing a liquid (24), the storage vessel comprising:
   a lower wall (22) and side walls (12);
   an arrangement for measuring the electrical conductivity of the liquid (24) located in the storage vessel (10), the arrangement comprising:
   (i) a first contact (20);
   (ii) a second contact (21),
   wherein the first contact (20) and the second contact (21) are wetted by the liquid (24) such that conductivity between the first and second contacts can be measured; and
   (iii) a first conductor loop (16) comprising an open conductor that is not closed and has two open ends, the two open ends comprising a first open end (18) and a second open end (19), the first conductor loop (16) being arranged between the first and second contacts such that the first open end (18) is electrically coupled to the first contact (20), and the second open end (19) is electrically coupled to the second contact (21); and
   a second conductor loop (26) configured and arranged with respect to the first conductor loop (16) to non-contactingly and inductively couple with the first conductor loop (16) to induce a voltage into the first conductor loop (16) by the inductive coupling, the second conductor loop (26) being directly coupled to an electronic measuring system (28) configured to determine and evaluate the current flow in the first conductor loop (16) and to determine the conductivity of the liquid on the basis of the determination and evaluation.

2. The storage vessel (10) as claimed in claim 1, wherein, the second conductor loop (26) is integrated into a housing (14), the housing (14) being separable from the storage vessel (10).

3. The storage vessel (10) as claimed in claim 2, wherein the storage vessel (10) comprises first guiding means (30) and the housing (14) comprises second guiding means (32), the first and second guiding means being configured to position the second conductor loop (26) in a pre-defined arrangement with respect to the first conductor loop (16).

4. The storage vessel (10) as claimed in claim 1, wherein the first and second contacts (20, 21) protrude into the liquid (24).

5. The storage vessel (10) as claimed in claim 1, wherein the first conductor loop (16) is embedded in the lower wall (22) of the storage vessel (10).

6. The storage vessel (10) as claimed in claim 1, wherein the lower wall (22) of the storage vessel (10) in the region of the first conductor loop (16) has a magnitude of electrical conductivity that is less than the magnitude of the electrical conductivity of the liquid (24) whose conductivity is to be measured.

7. The storage vessel (10) as claimed in claim 1, wherein the first and the second conductor loops (16, 26) each comprise a longitudinal axis and the longitudinal axes are arranged in an operating position parallel to one another.

8. The storage vessel (10) as claimed in claim 1, wherein the first conductor loop (16) and the second conductor loop (26) are arranged coaxially with respect to one another in an operating position.

9. The storage vessel (10) as claimed in claim 1, wherein the storage vessel (10) is a tank in a vehicle.

10. The storage vessel (10) as claimed in claim 1, wherein the storage vessel (10) is provided in an SCR system.

11. A method for measuring the conductivity of a liquid in a storage vessel for storing a liquid (24), the storage vessel having:
    a lower wall (22) and side walls (12);
    an arrangement for measuring the electrical conductivity of the liquid (24) located in the storage vessel (10), the arrangement comprising:
    (i) a first contact (20);
    (ii) a second contact (21),
    wherein the first contact (20) and the second contact (21) are wetted by the liquid (24) such that conductivity between the first and second contacts can be measured; and
    (iii) a first conductor loop (16) comprising an open conductor that is not closed and has two open ends, the two open ends comprising a first open end (18) and a second open end (19), the first conductor loop (16) being arranged between the first and second contacts such that the first open end (18) is electrically coupled to the first contact (20), and the second open end (19) is electrically coupled to the second contact (21); and
    a second conductor loop (26) configured and arranged with respect to the first conductor loop (16) to non-contactingly and inductively couple with the first conductor loop (16) to induce a voltage into the first conductor loop (16) by the inductive coupling, the second conductor loop (26) being directly coupled to an electronic measuring system (28) configured to determine and evaluate the current flow in the first conductor loop (16) and to determine the conductivity of the liquid on the basis of the determination and evaluation, the method comprising:
    inducing a voltage into the first conductor loop (16) by generating a magnetic field using the second conductor loop (26); and
    determining the conductivity of the liquid (24) by evaluating an induction current in the first conductor loop (16), the evaluation of the induction current being performed by the electronic measuring system (28) coupled to the second conductor loop (26).

* * * * *